US008865892B2

(12) United States Patent
Tsai et al.

(10) Patent No.: US 8,865,892 B2
(45) Date of Patent: Oct. 21, 2014

(54) CATALYST COMPOSITION AND METHOD FOR PREPARING AMIDE USING THE SAME

(75) Inventors: Tung-Han Tsai, Taipei (TW); Cheng-Fa Hsieh, Taipei (TW); Hung-Hung Hseuh, Taipei (TW); Chien-Chuan Shih, Taipei (TW)

(73) Assignee: China Petroleum Development Corporation, Taipei (Taiwan), Taipei (TW)

( * ) Notice: Subject to any disclaimer, the term of this patent is extended or adjusted under 35 U.S.C. 154(b) by 0 days.

(21) Appl. No.: 13/332,834

(22) Filed: Dec. 21, 2011

(65) Prior Publication Data

US 2012/0184733 A1    Jul. 19, 2012

(30) Foreign Application Priority Data

Jan. 17, 2011 (TW) .............................. 100101602 A

(51) Int. Cl.
*C07D 201/04* (2006.01)
*B01J 31/02* (2006.01)
*C07C 231/10* (2006.01)

(52) U.S. Cl.
CPC ............ *C07D 201/04* (2013.01); *B01J 31/0237* (2013.01); *B01J 2231/52* (2013.01); *C07C 231/10* (2013.01); *B01J 31/0244* (2013.01)
USPC ........................................................ 540/535

(58) Field of Classification Search
USPC ........................................................ 540/535
See application file for complete search history.

(56) References Cited

U.S. PATENT DOCUMENTS 3,904,609 A   9/1975 Mattone et al.
3,912,721 A   10/1975 Mattone et al.
6,265,574 B1   7/2001 Kitamura et al.

*Primary Examiner* — Bruck Kifle
(74) *Attorney, Agent, or Firm* — Edwards Wildman Palmer LLP; Peter F. Corless; Richard B. Emmons

(57) ABSTRACT

The present invention provides a method for preparing an amide. The method includes the steps of performing in a reactor including a catalyst composition having a nitrogen-containing heterocyclic compound and sulfuric acid Beckman rearrangement of a ketoxime to form a product stream having the amide, wherein a molar ratio of the nitrogen-containing heterocyclic compound to the sulfuric acid is from 1:1 to 1:8; and separating an organic phase having the amide and an aqueous phase having the catalyst composition from the product stream. The present invention facilitates the regeneration of the catalyst composition with low water content, so as to increase the conversion rate of a ketoxime and the selectivity of an amide.

8 Claims, No Drawings

CATALYST COMPOSITION AND METHOD FOR PREPARING AMIDE USING THE SAME

CROSS-REFERENCES TO RELATED APPLICATIONS

This application claims under 35 U.S.C. §119(a) the benefit of Taiwanese Application No. 100101602, filed Jan. 17, 2011, the entire contents of which is incorporated herein by reference.

BACKGROUND OF THE INVENTION

1. Field of the Invention

The present invention relates to methods for preparing amides, and more particularly, to a method using a catalyst composition for preparing an amide.

2. Description of the Prior Art

Caprolactam is an important raw material in the manufacture of nylon 6 fibers and thin films. Beckman rearrangement of cyclohexanone oxime is an important reaction step in producing caprolactam. Currently, oleum is used as a catalyst for converting cyclohexanone oxime to caprolactam sulfate during Beckman rearrangement, and then ammonia is used for neutralization, so as to obtain caprolactam. While the conversion rate of cyclohexanone oxime is almost 100% and the selectivity for caprolactam is 99%, a large amount of low-valued ammonium sulfate is generated during the reaction, and concentrated sulfuric acid used for catalysis causes problems such as corrosion to the whole equipment and environmental pollution. In recent years, researches on new production technologies of caprolactam focus on reducing or avoiding the generation of the by-product, ammonium sulfate. U.S. Pat. No. 6,265,574 discloses subjecting cyclohexanone oxime to a gaseous phase Beckmann rearrangement reaction in a fluidized bed system, wherein there is no byproduct, ammonium sulfate, produced in the gaseous conversion reaction, but selectivity of caprolactam is only 95.7%, and the reaction temperature (300-350° C.) is higher than that of liquid phase reaction. In addition, the major disadvantage of the gaseous conversion reaction is that the catalyst is easily inactive, and thus the regeneration of the catalyst is frequently required, which is disadvantageous to the long term continuous operation.

U.S. Pat. No. 3,912,721 and U.S. Pat. No. 3,904,609 disclose the extraction of amides in an acid and the subsequent purification, wherein caprolactam is recovered by an extraction agent to a specific group. However, during the extraction of amides, water needs to be added to oleum, and it is hard to remove the water during the process. If sulfuric acid contains too much water, cyclohexanone oxime would be hydrolyzed in the conversion reaction to form cyclohexanone, and thus the selectivity is significantly reduced. Therefore, oleum in such method cannot be regenerated.

Hence, there is a need to develop a liquid phase rearrangement of a ketoxime for preparing an amide, wherein the method has a high conversion rate of a ketoxime, a high selectivity of an amide and regeneration of a catalyst.

SUMMARY OF THE INVENTION

The present invention provides a catalyst composition, which may be regenerated, and provides a method for preparing an amide by using the catalyst composition.

The present invention provides a catalyst composition for preparing an amide, and the catalyst composition includes a nitrogen-containing heterocyclic compound and a sulfuric acid, wherein a molar ratio of the nitrogen-containing heterocyclic compound to the sulfuric acid is from 1:1 to 1:8.

Further, the present invention provides a method for using the catalyst composition. In the method, Beckman rearrangement of a ketoxime is performed and catalyzed by the catalyst composition in a reactor to form a product stream having an amide; and an organic phase having the amide and an aqueous phase dissolving the catalyst composition are separated from the product stream.

The catalyst composition of the present invention facilitates the regeneration thereof and reduction of water content of the catalyst composition. Therefore, the method of the present invention further includes the steps of dehydrating the aqueous phase to obtain the dehydrated catalyst composition, and then introducing the dehydrated catalyst composition to the reactor.

In the present invention, the nitrogen-containing heterocyclic compound is one or more selected from the group consisting of a compound of formula (I), a compound of formula (II) in a combination thereof:

wherein each circle is one of 5-member to 10-member rings and has one or more nitrogen atoms, and $R_1$ and $R_2$ are independently hydrogen or $C_1$-$C_8$alkyl, in which $C_1$-$C_8$alkyl is unsubstituted or substituted with —OH, —COOH, $NH_2C$(=NH)NH—, —$NH_2$, —$CONH_2$, —COOR, in which is R is $C_1$-$C_8$alkyl, —$SO_3H$, ClSO—, hydroxyphenyl, $C_1$-$C_8$alkylthio, —SH, $C_6$-$C_{10}$aryl, or 5- to 10-member heteroaryl including at least one heteroatom selected from N, S or O.

In one embodiment, the nitrogen-containing heterocyclic compound is a 5-member ring or a 6-member ring, and has one or two nitrogen atoms. The nitrogen-containing heterocyclic compound is one or more selected from the group consisting of N-methylimidazole, pyridine, piperidine and pyrrolidine.

After Beckman rearrangement of a ketoxime is catalyzed by the catalyst composition to form an amide, water is added in the reaction, the product stream is extracted by an organic solvent such alkyl phenol or aromatic alcohol, the amide is extracted from the aqueous phase to the organic phase, and the amide is separated from the extraction agent by distillation. The water content of the catalyst composition dissolved in the aqueous phase is reduced to the low water content by reduced pressure evaporation or distillation at 80 to 180° C., and the catalyst composition is regenerated.

In comparison with conventional method using oleum to prepare an amide, the catalyst composition and the method for preparing an amide in the present invention have the advantages of: (1) The water content of the catalyst composition having a nitrogen-containing heterocyclic compound and a sulfuric acid may be easily reduced to low water content, and the catalyst composition may be regenerated by dehydrating the catalyst composition to have low water content after extracting the amide; and (2) No by product, ammonium sulfate is produced.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides a catalyst composition for preparing an amide, and the catalyst composition includes a nitrogen-containing heterocyclic compound and a sulfuric acid. The sulfuric acid generally has 2 wt % of water, oleum is not necessary, and a nitrogen-containing heterocyclic compound is used to achieved high selectivity (98%). The molar ratio of the nitrogen-containing heterocyclic compound to the sulfuric acid is from 1:1 to 1:8, preferably 1:1 to 1:5, and more preferably 1:1 to 1:3.

For example, the nitrogen-containing heterocyclic compound is one or more selected from the group consisting of a compound of formula (I), a compound of formula (II) and a combination thereof:

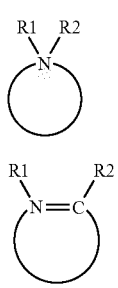

wherein each circle is one of 5-member to 10-member rings and has one or more nitrogen atoms, and $R_1$ and $R_2$ are independently hydrogen or $C_1$-$C_8$alkyl, in which $C_1$-$C_8$alkyl is unsubstituted or substituted with —OH, —COOH, $NH_2C$(=NH)NH—, —$NH_2$, —$CONH_2$, —COOR, in which is R is $C_1$-$C_8$alkyl, —$SO_3H$, ClSO—, hydroxyphenyl, $C_1$-$C_8$alkylthio, —SH, $C_6$-$C_{10}$aryl, or 5- or 10-member heteroaryl.

In an embodiment, the nitrogen-containing heterocyclic compound is a 5-member ring or a 6-member ring, and has one or two nitrogen atoms. For example, nitrogen-containing heterocyclic compound is one or more selected from the group consisting of N-methylimidazole, pyridine, piperidine and pyrrolidine.

The present invention further provides a method for preparing an amide. The method includes the steps of performing Beckman rearrangement of a ketoxime to form a product stream having an amide in a reactor including a catalyst composition having a nitrogen-containing heterocyclic compound and a sulfuric acid, wherein a mole ratio of the nitrogen-containing heterocyclic compound to the sulfuric acid is from 1:1 to 1:8; and separating an organic phase having an amide and an aqueous phase having the catalyst composition from the product stream.

In the present invention, the ketoxime is one selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime. The reaction is performed in an organic solvent such as toluene at 80 to 140° C., preferably 90 to 120° C. and more preferably 100 to 115° C. After the product stream is extracted, the aqueous phase is dehydrated to obtain the dehydrated catalyst composition; and then the dehydrated catalyst composition is introduced into the reactor for reuse. Generally, after the aqueous phase is dehydrated by reduced pressure evaporation or distillation, the water content of the dehydrated catalyst composition may be reduced to be lower than 0.1 wt %.

Embodiments 1-3

0.1 mol of N-methylimidazole and the specified amount of sulfuric acid were placed into a flask. The initial water content was 10 wt %. The reduced pressure evaporation was performed at 8 mbar and 140° C. After 2 hours, the final water content was determined by Mettler DL31 titrator. The results were shown in Table 1.

TABLE 1

| Embodiment | N-methylimidazole/sulfuric acid (mol) | Final water content (wt %) |
|---|---|---|
| 1 | 1:2 | 0.01 |
| 2 | 1:4 | 0.31 |
| 3 | 1:8 | 1.32 |

Comparative Example 1

0.2 mol of sulfuric acid was placed in a flask. The initial water content was 10%. The reduced pressure evaporation was performed at 8 mbar and 140° C. After 2 hours, the final water content was determined by Mettler DL31 titrator. The results were shown in Table 2.

TABLE 2

| Comparative Example | N-methylimidazole/sulfuric acid (mol) | Final water content (wt %) |
|---|---|---|
| 1 | Sulfuric acid only | 2.31 |

Embodiments 4-7

0.1 mol of N-methylimidazole and 0.4 mol of sulfuric acid were placed into a flask. The initial water content was 10 wt %. The reduced pressure evaporations were performed at 8 mbar and different temperatures. After 2 hours, the final water content was determined. The results were shown in Table 3.

TABLE 3

| Embodiment | N-methylimidazole/sulfuric acid (mol) | Temperature (° C.) | Final water content (wt %) |
|---|---|---|---|
| 4 | 1:4 | 90 | 1.2 |
| 5 | 1:4 | 110 | 0.77 |
| 6 | 1:4 | 140 | 0.31 |
| 7 | 1:4 | 160 | 0.21 |

Embodiments 8-11

0.1 mol of the nitrogen-containing heterocyclic compound listed in Table 4 and 0.2 mol of sulfuric acid were placed in a flask. The initial water content was 10 wt %. The reduced pressure evaporation was performed at 8 mbar and 95° C. After 2 hours, the final water content was determined. The results were shown in Table 4.

TABLE 4

| Embodiment | Nitrogen-containing heterocyclic compound | Final water content (wt %) |
| --- | --- | --- |
| 8 | N-methylimidazole | 0.16 |
| 9 | pyridine | 0.13 |
| 10 | piperidine | 0.18 |
| 11 | pyrrolidine | 0.2 |

The following embodiments illustrate that the catalyst composition of the present invention is used for Beckman rearrangement of a ketoxime to form an amide.

Embodiments 12 and 13

The dehydrated catalyst composition in Embodiments 1-2 was placed in a flask, and added with 50 ml of toluene. The mixture was stirred, heated to 110° C., and then added with 0.05 mol of cyclohexanone oxime. The reaction was performed for 0.5 hour, and then the toluene was separated from the reaction liquid. The reaction liquid was added with 15 ml of water, and then extracted by t-butylphenol, so that the amide was extracted from the aqueous phase to the organic phase. The organic phase on the upper layer was analyzed by gas chromatography to determine the conversion rate of the reactant and the selectivity of the product. The results were shown in Table 5.

The conversion rate of a ketoxime and the selectivity of an amide are calculated as follows.

Conversion rate(%)=(moles of consumed ketoxime/initial moles of ketoxime)×100%

Selectivity(%)=(moles of produced amide/moles of consumed ketoxime)×100%

TABLE 5

| Embodiment | N-methylimidazole/sulfuric acid (mol) | Conversion rate of ketoxime | Selectivity of amide |
| --- | --- | --- | --- |
| 12 | 1:2 | 99% | 98% |
| 13 | 1:4 | 99% | 97% |

Comparative Example 2

Sulfuric acid was placed in a flask as Comparative Example 1, and then added with 50 mol of toluene. The mixture was stirred, heated to 110° C., and then added with 0.05 mol of cyclohexanone oxime. The reaction was performed for 0.5 hour, and then the toluene was separated from the reaction liquid. The reaction liquid was added with 15 ml of water, and then extracted by t-butylphenol, so that the amide was extracted from the aqueous phase to the organic phase. The organic phase on the upper layer was analyzed by gas chromatography to determine the conversion rate of the reactant and the selectivity of the product. The results were shown in Table 6.

TABLE 6

| Comparative Example | N-methylimidazole/sulfuric acid (mol) | Conversion rate of ketoxime | Selectivity of amide |
| --- | --- | --- | --- |
| 2 | Sulfuric acid only | 100% | 92% |

The following embodiment illustrates the reuse of the catalyst composition for Beckman rearrangement of a ketoxime to form an amide.

Embodiment 14

250 ml of the composition as Embodiment 1 was placed in a flask, and added with 50 ml of toluene. The mixture was stirred, heated to 110° C., and then added with 0.05 mol of cyclohexanone oxime. The reaction was performed for 0.5 hour, and then the toluene was separated from the reaction liquid. The reaction liquid was added with 15 ml of water, and then extracted by t-butylphenol, so that the amide was extracted from the aqueous phase to the organic phase. The organic phase on the upper layer was analyzed by gas chromatography to determine the conversion rate of the reactant and the selectivity of the product. The catalyst composition dissolved in the aqueous phase was regenerated by reduced pressure evaporation at 8 mbar and 140° C. The above procedure was repeated for multiple times. The results were shown in Table 7.

TABLE 7

| Embodiment | Reaction | Conversion rate of ketoxime | Selectivity of amide |
| --- | --- | --- | --- |
| 14 | First time reaction | 99% | 98% |
|  | Second time reaction | 99% | 98% |
|  | Third time reaction | 99% | 98% |
|  | Fourth time reaction | 98.9% | 98% |

Accordingly, the catalyst composition having a nitrogen-containing heterocyclic compound and a sulfuric acid can be regenerated for Beckman rearrangement of a ketoxime to form an amide, and have high reactivity and selectivity.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing a lactam, comprising the steps of:
    performing in a reactor containing a catalyst composition having one or more nitrogen-containing heterocyclic compound selected from the group consisting of N-methylimidazole, pyridine, piperidine and pyrrolidine and sulfuric acid Beckman rearrangement of a ketoxime to form a product stream having the lactam, wherein a molar ratio of the nitrogen-containing heterocyclic compound to the sulfuric acid is from 1:1 to 1:8; and
    separating an organic phase having the lactam and an aqueous phase having the catalyst composition from the product stream,
    wherein the lactam is caprolactam.

2. The method of claim 1, further comprising the steps of:
dehydrating the aqueous phase to form a dehydrated catalyst composition; and
introducing the dehydrated catalyst composition into the reactor.

3. The method of claim 2, wherein the aqueous phase is dehydrated by reduced pressure evaporation or distillation, so as to reduce water content of the catalyst composition to be lower than 0.1 wt %.

4. The method of claim 3, wherein the aqueous phase is dehydrated at 80 to 180° C.

5. The method of claim 1, wherein the mole ratio of the nitrogen-containing heterocyclic compound to the sulfuric acid is from 1:1 to 1:5.

6. The method of claim 1, wherein the ketoxime is one selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime.

7. The method of claim 1, wherein the Beckman rearrangement is performed at 80 to 140° C.

8. The method of claim 1, wherein the Beckman rearrangement is performed in the presence of an organic solvent.

* * * * *